(12) United States Patent
Takayanagi et al.

(10) Patent No.: US 10,376,713 B2
(45) Date of Patent: Aug. 13, 2019

(54) RADIATION THERAPY PLANNING SYSTEM, RADIATION THERAPY PLANNING METHOD, AND RADIATION THERAPY SYSTEM

(71) Applicant: HITACHI, LTD., Tokyo (JP)

(72) Inventors: Taisuke Takayanagi, Tokyo (JP);
Shusuke Hirayama, Tokyo (JP);
Shinichiro Fujitaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 111 days.

(21) Appl. No.: 15/513,276

(22) PCT Filed: May 12, 2015

(86) PCT No.: PCT/JP2015/063689
§ 371 (c)(1),
(2) Date: Mar. 22, 2017

(87) PCT Pub. No.: WO2016/047194
PCT Pub. Date: Mar. 31, 2016

(65) Prior Publication Data
US 2017/0304651 A1 Oct. 26, 2017

(30) Foreign Application Priority Data
Sep. 24, 2014 (JP) ................................. 2014-193472

(51) Int. Cl.
*A61N 5/10* (2006.01)

(52) U.S. Cl.
CPC ............. *A61N 5/1031* (2013.01); *A61N 5/10* (2013.01); *A61N 5/1043* (2013.01); *A61N 2005/1034* (2013.01); *A61N 2005/1087* (2013.01)

(58) Field of Classification Search
CPC ...... A61N 5/10; A61N 5/1031; A61N 5/1043; A61N 2005/1087; A61N 2005/1034
See application file for complete search history.

(56) References Cited

U.S. PATENT DOCUMENTS

| 2009/0175418 | A1 | 7/2009 | Sakurai et al. |
| 2013/0102830 | A1* | 4/2013 | Otto ..................... A61N 5/1031 600/1 |
| 2014/0235923 | A1 | 8/2014 | McNutt et al. |

FOREIGN PATENT DOCUMENTS

| JP | 2002-336365 A | 11/2002 |
| JP | 2004-041292 A | 2/2004 |

(Continued)

OTHER PUBLICATIONS

Ryosuke Kohno, et al. "Simplified Monte Carlo Dose Calculation for Therapeutic Proton Beams" Jpn. J. Appl. Phys. vol. 41 (2002) pp. L294-L297.

(Continued)

*Primary Examiner* — Christine H Matthews
*Assistant Examiner* — Joshua Daryl D Lannu
(74) *Attorney, Agent, or Firm* — Mattingly & Malur, PC

(57) ABSTRACT

A radiation therapy planning apparatus performs dose calculation at high speed and with high accuracy for radiation therapy in a scanning irradiation method. The apparatus includes a display, an arithmetic processing apparatus, a memory, and a data server, which is connected to a particle beam irradiation apparatus. A dose calculation unit of the arithmetic processing apparatus calculates dose distribution by a simplified Monte Carlo algorithm, and corrects the dose distribution by a decreasing rate stored in a particle number decreasing rate table of the memory, and stores the corrected dose distribution in an integrated dose distribution table. By using the simplified Monte Carlo algorithm and the particle number decreasing rate that corrects the simplified Monte (Continued)

Carlo algorithm, the dose distribution is calculated, and thereby, it is possible to realize a radiation therapy planning apparatus that performs dose calculation at a high speed with high accuracy.

14 Claims, 10 Drawing Sheets

(56) References Cited

FOREIGN PATENT DOCUMENTS

| JP | 2004041292 A | * | 2/2004 |
|---|---|---|---|
| JP | 2009-160309 A | | 7/2009 |
| JP | 2010-057656 A | | 3/2010 |
| JP | 2013-248133 A | | 12/2013 |
| JP | 2014-528797 A | | 10/2014 |

OTHER PUBLICATIONS

Yupeng Li, et al. "Beyond Gaussians: a study of single-spot modeling for scanning proton dose calculation" Phys. Med. Biol. 57 (2012), pp. 983-997.

International Search Report of PCT/JP2015/063689 dated Aug. 4, 2015.

International Preliminary Report on Patentability received in corresponding International Application No. PCT/JP2015/063689 dated Apr. 6, 2017.

* cited by examiner

[Fig. 1]
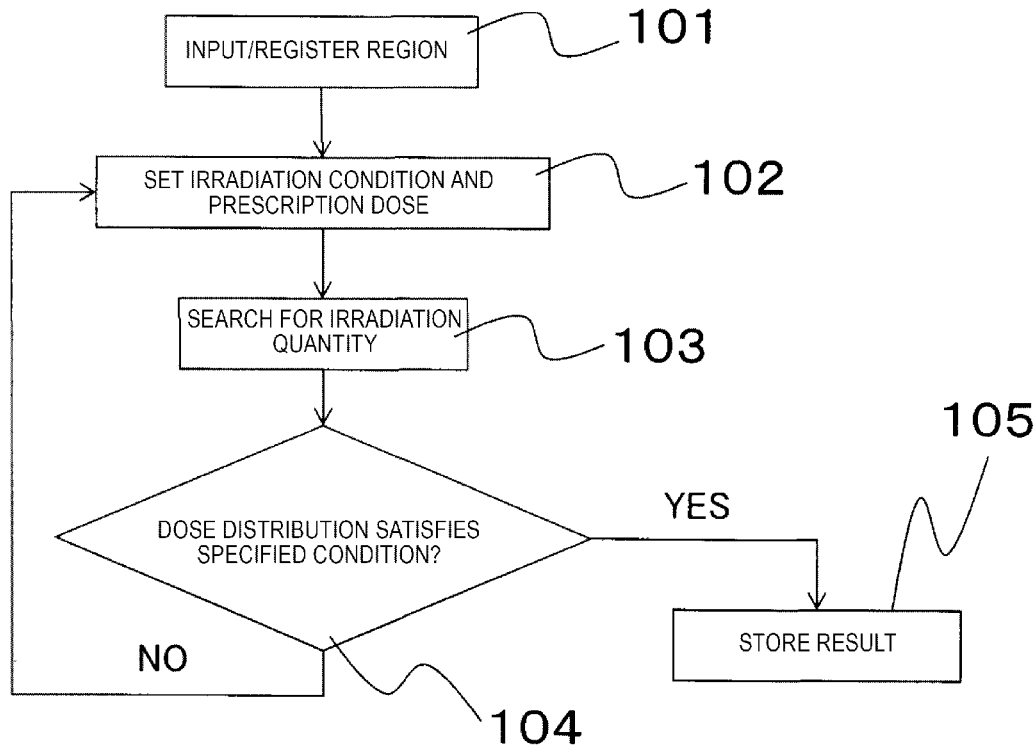
[Fig. 2]
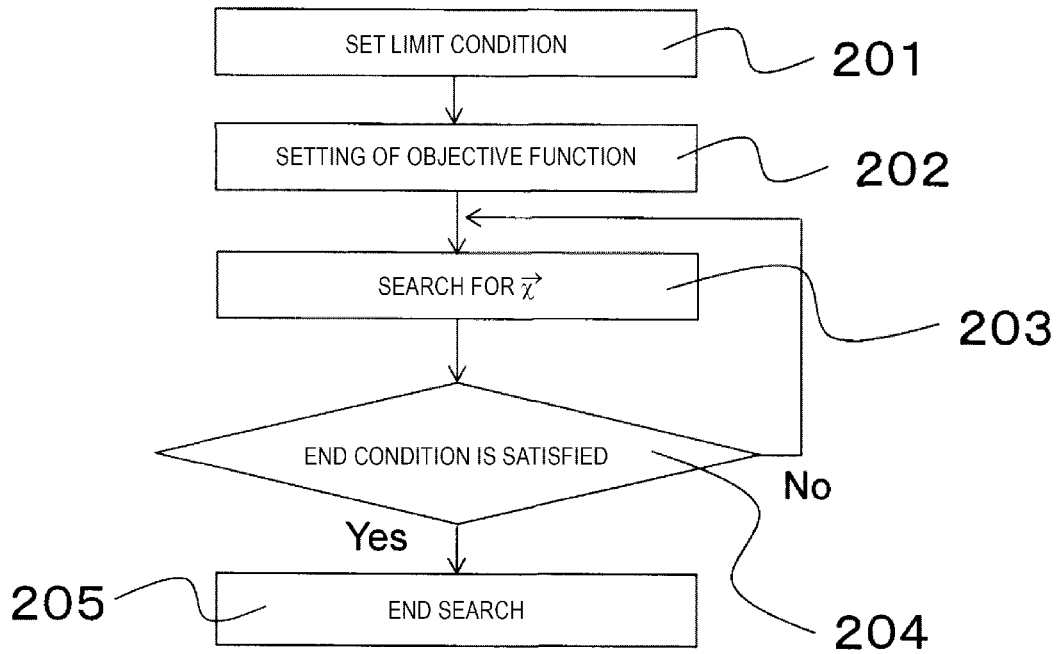

[Fig. 3]
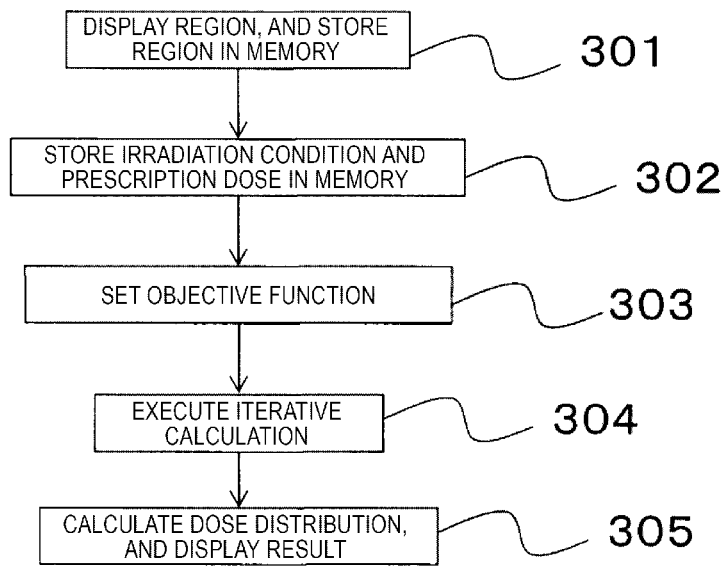

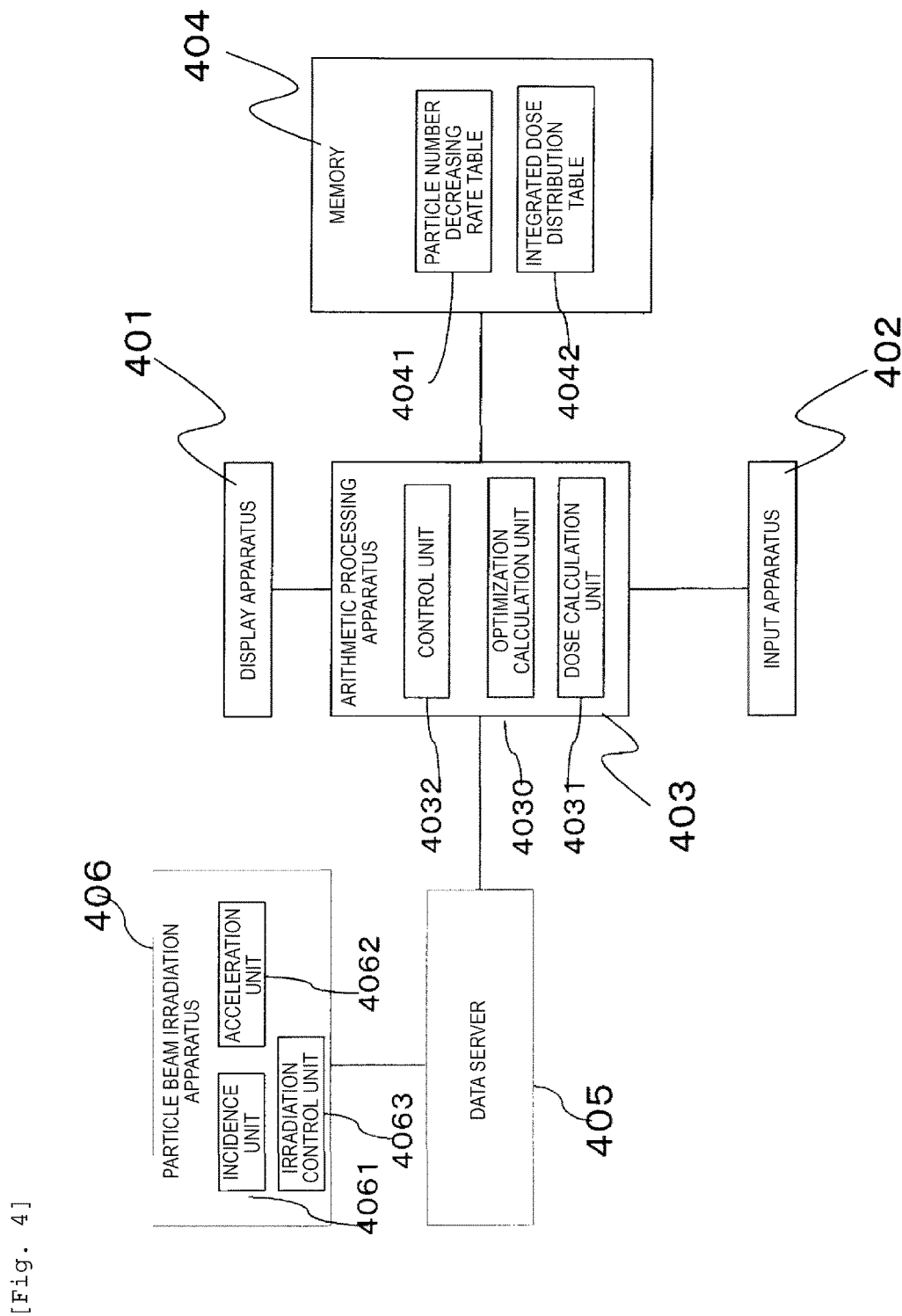
[Fig. 4]

[Fig. 5]
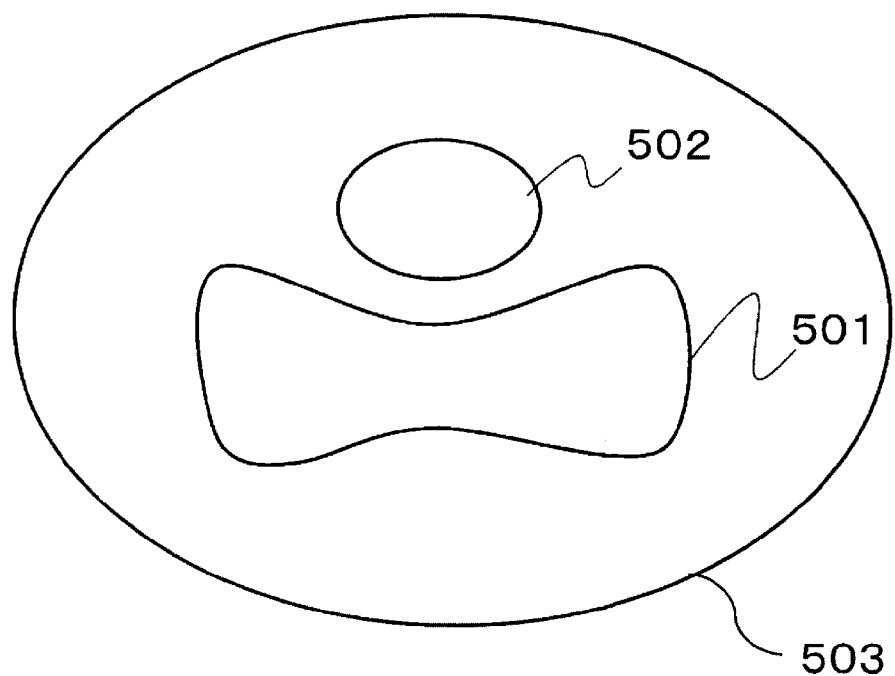

[Fig. 6]
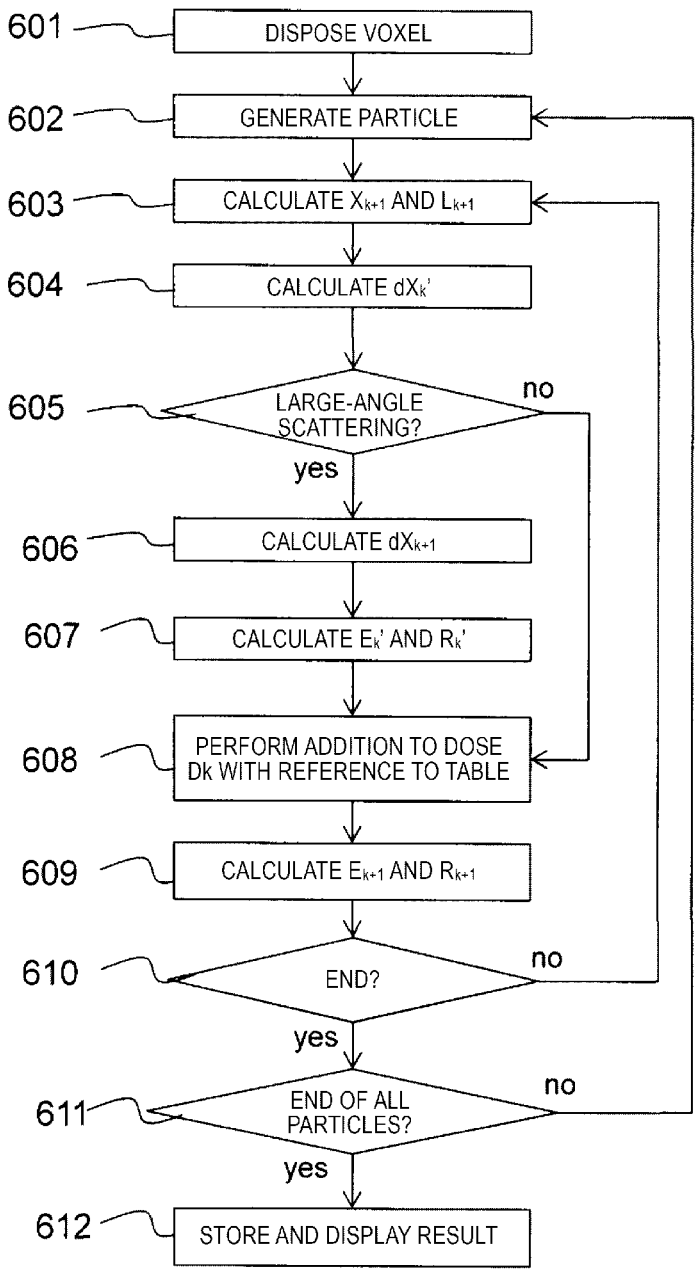

[Fig. 7]
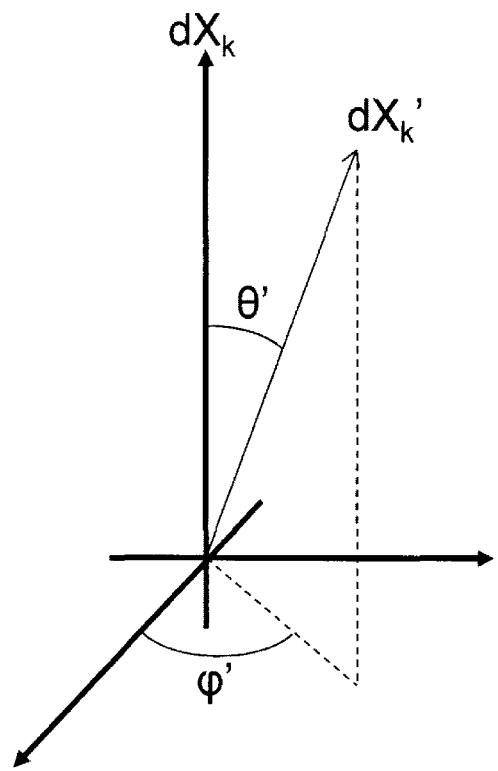
[Fig. 8]
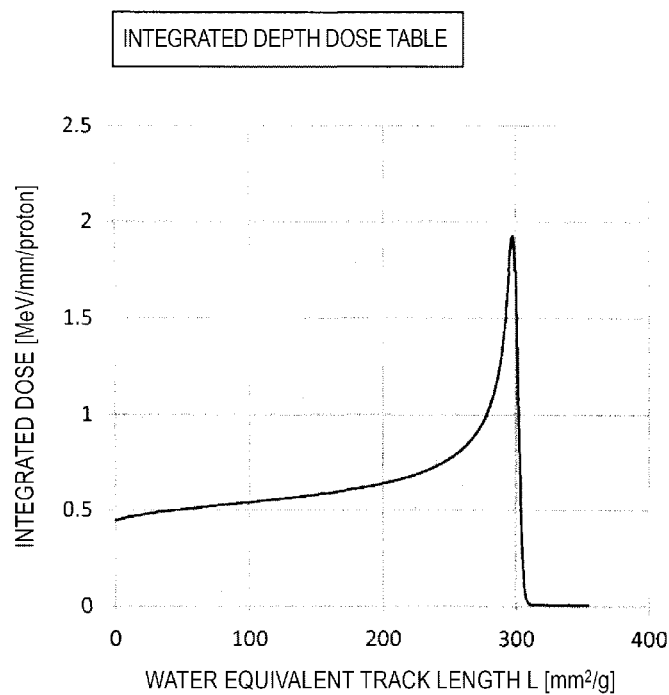

[Fig. 9]
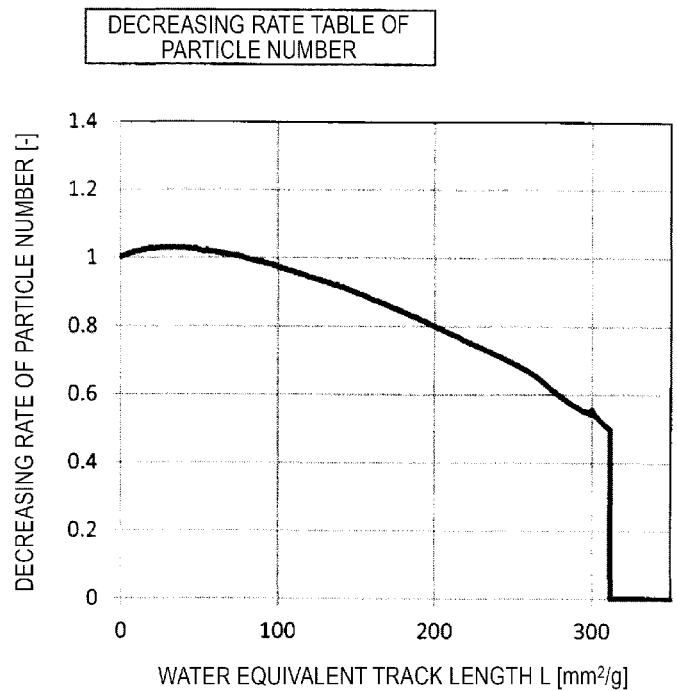
[Fig. 10]
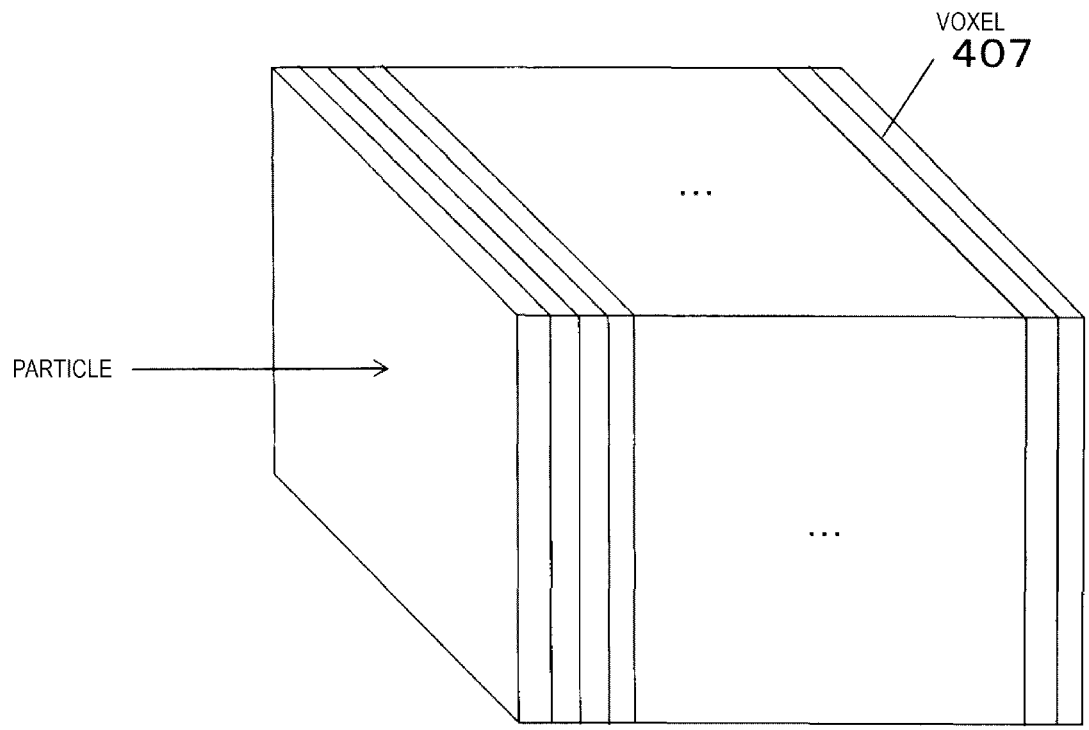

[Fig. 11]
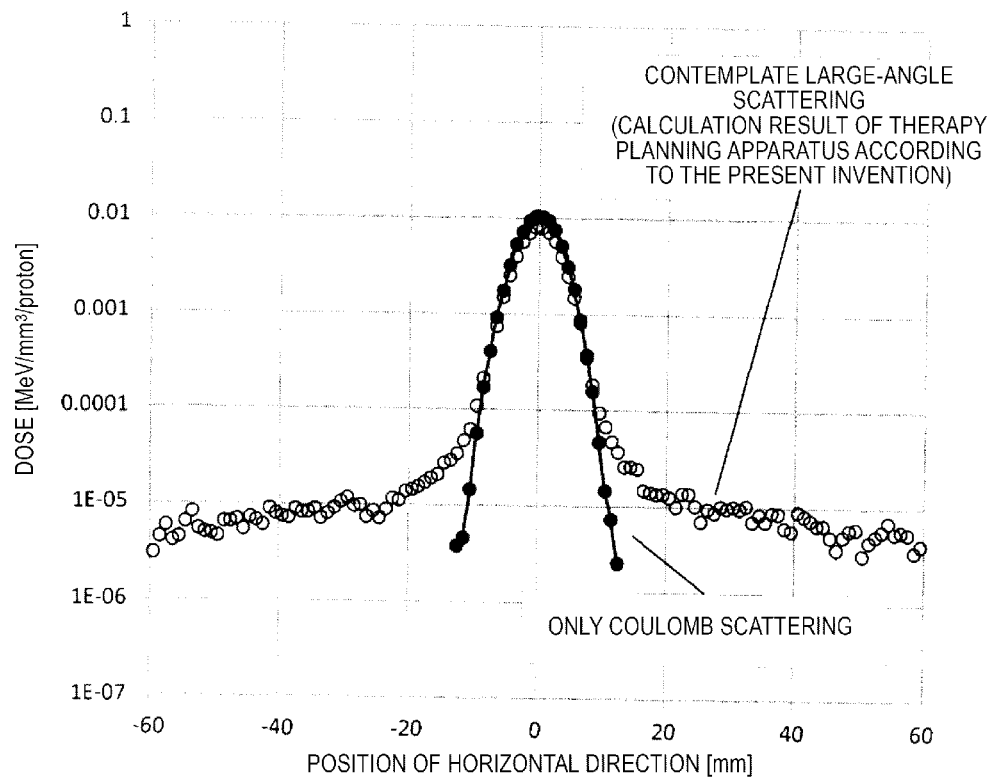
[Fig. 12]
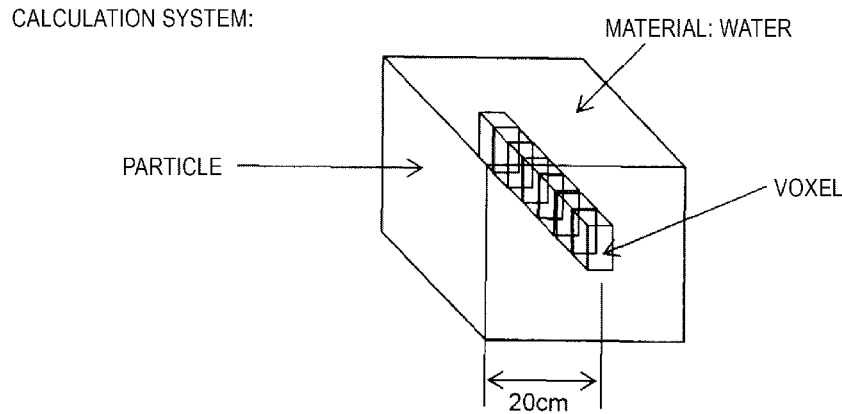

[Fig. 13]
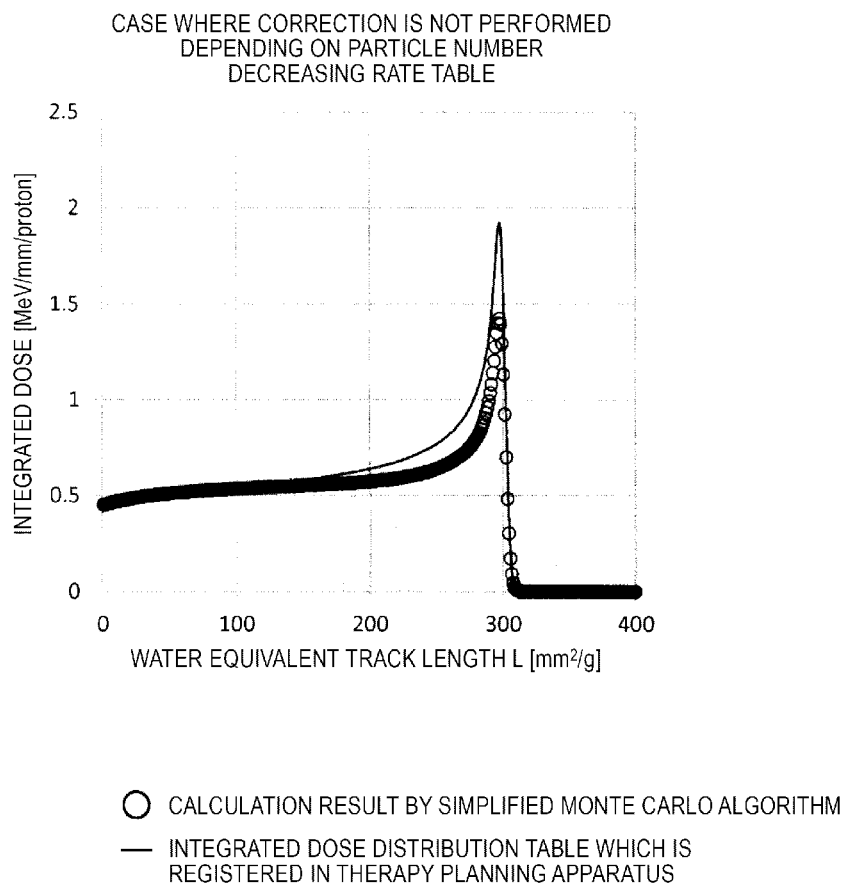

[Fig. 14]
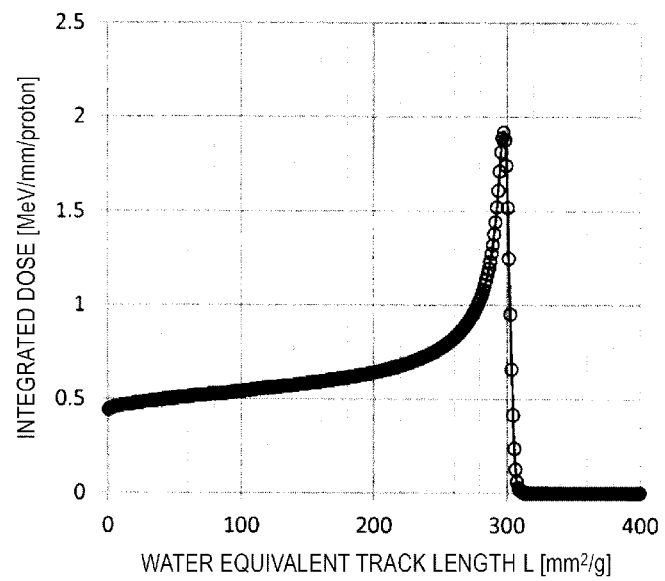

RADIATION THERAPY PLANNING SYSTEM, RADIATION THERAPY PLANNING METHOD, AND RADIATION THERAPY SYSTEM

TECHNICAL FIELD

The present invention relates to a radiation therapy planning apparatus, a radiation therapy planning method, and a radiation therapy apparatus.

BACKGROUND ART

In a therapy using radiation, increased is a demand for a particle beam therapy apparatus using a particle beam (charged particle beam) that is represented by a proton beam or a carbon ion beam having high dose concentration ability on a tumor cell to be a target.

Even in the particle beam therapy apparatus, there is a need to irradiate a tumor region with a specified dose so as to concentrate the dose on the tumor region as precisely as possible. As a method for concentrating the dose in the particle beam therapy, use of a scanning method is widely spread. The scanning method is a method in which an inside of the tumor is irradiated so as to be fully filled by guiding a fine particle beam to an arbitrary position within a plane, and a high dose is assigned only to the tumor region. In a case of the scanning method, there is basically no need for a patient-specific instrument such as a collimator, and there is an advantage to be capable of variously forming distribution.

A radiation therapy planning apparatus is an apparatus that simulates dose distribution in a body of a patient by numerical value calculation, based on information in the body of the patient obtained from a CT image or the like. An operator determines irradiation conditions such as an irradiation direction of the particle beam, beam energy, an irradiation position and an irradiation quantity while referring to a calculation result of the therapy planning apparatus. Hereinafter, a general process thereof will be briefly described. In the scanning irradiation, there are a spot scanning method and a raster method, but here, a case on the assumption of the spot scanning method will be described.

First, the operator inputs a target region to be irradiated with the radiation. If necessary, the operator similarly inputs and registers a position of an important organ where the irradiation quantity of the radiation is suppressed to be low as far as possible.

Next, the operator sets a prescription dose which becomes a dose value to be an aim with respect to each of the registered regions.

Subsequently, the irradiation condition realizing the dose distribution which satisfies the prescription dose is determined. The operator adjusts a parameter relating to the irradiation condition to be determined by using the therapy planning apparatus until the dose distribution which is contemplated to be proper is obtained. In order to efficiently determine the parameter, a method for using an objective function that quantifies a deviation from the prescription dose is widely adopted.

As one of a method for calculating the dose distribution of the proton beam in the therapy planning apparatus, there is a simplified Monte Carlo algorithm (NPL 1). In the simplified Monte Carlo algorithm, since transport calculation is performed with respect to beam particles one by one in the same manner as a normal Monte Carlo algorithm, it is possible to calculate the dose distribution with high accuracy in a nonhomogeneous medium.

In the transport calculation, trajectories of the particles are dividedly connected to minute steps, and in each step, a very small change is given in a track direction depending on multiple Coulomb scattering. A scattering angle of the multiple Coulomb scattering is modeled by a random number of Gaussian distribution, and a standard deviation thereof is calculated per step by using Highland's formula or the like.

Here, in NPL 2, written is a need to contemplate a dose component due to the particles which are scattered at a large angle by a nuclear reaction or the like, in order to secure sufficient calculation accuracy, in the dose calculation of a scanning irradiation method.

CITATION LIST

Non Patent Literature

NPL 1: Ryosuke KOHNO, et al. "Simplified Monte Carlo Dose Calculation for Therapeutic Proton Beams" Jpn. J. Appl. Phys. Vol. 41 (2002) pp. L294-L297

NPL 2: Yupeng Li, et al. "Beyond Gaussians: a study of single-spot modeling for scanning proton dose calculation" Phys. Med. Biol. 57 (2012) 983-997

SUMMARY OF INVENTION

Technical Problem

In the radiation therapy of the scanning irradiation method, a radiation therapy planning apparatus that enables to perform dose calculation at a high speed and with high accuracy is desired.

Here, the simplified Monte Carlo algorithm described above is contemplated to be applied to dose distribution calculation of the scanning irradiation method. As illustrated in NPL 2, in order to obtain the sufficient accuracy in the dose calculation of the scanning irradiation method, it is necessary to reproduce the dose of a region separated from a center of the beam. Therefore, there is a need to contemplate a phenomenon in which the particles are scattered in the direction of the larger angle by elastic scattering or inelastic scattering with an atomic nucleus, in addition to the multiple Coulomb scattering of which the scattering angle is approximated to Gaussian distribution.

However, if such a large-angle scattering phenomenon is incorporated into the simplified Monte Carlo algorithm described above, on the contrary, degradation of the dose calculation accuracy may be caused. This is made because storing of the number of particles with respect to the track direction of the beam is not valid. Since energy of the particles is locally lost in the large-angle scattering, a range of the particles becomes short in comparison with the particles which are not scattered at a large angle. Therefore, if being incorporated into the dose calculation, the number of particles is decreased depending on the track direction of the beam.

Even if the normal Monte Carlo algorithm is contemplated to be applied to the dose distribution calculation of the scanning irradiation method, as described above, in the normal Monte Carlo algorithm, a speed of the dose calculation is low, and the calculation time becomes long as approximately one order in comparison with the simplified Monte Carlo algorithm.

Therefore, in a case where the normal Monte Carlo algorithm is applied to the dose distribution calculation of the scanning irradiation method, it is difficult to perform the dose calculation at a high speed.

An object of the present invention is to realize a radiation therapy planning apparatus, a radiation therapy planning method, and a radiation therapy system that enable to perform dose calculation at a high speed and with high accuracy, in a radiation therapy of a scanning irradiation method.

Solution to Problem

In order to achieve the object, the present invention is configured as follows.

There is provided a radiation therapy planning apparatus including an input unit where a target region and a prescription dose of an irradiated body which is irradiated with radiation are input, a memory where a radiation decreasing rate table indicating a relationship between a track length of the radiation to the irradiated body and a decreasing rate of the radiation is stored, and an arithmetic processing unit that calculates dose distribution by a simplified Monte Carlo algorithm, based on the target region and the prescription dose of the irradiated body input from the input unit, and corrects the calculated dose distribution by using the decreasing rate of the radiation of the radiation decreasing rate table stored in the memory. The dose distribution which is calculated and corrected in the arithmetic processing is stored in the memory.

There is provided a radiation therapy planning method including inputting a target region and a prescription dose of an irradiated body which is irradiated with radiation to an input unit, calculating dose distribution by a simplified Monte Carlo algorithm, based on the target region and the prescription dose of the irradiated body input from the input unit, and correcting the calculated dose distribution by using a decreasing rate of the radiation stored in a radiation decreasing rate table indicating a relationship between a track length of the radiation and the decreasing rate of the radiation, and storing the corrected dose distribution in a memory.

There is provided a radiation therapy system including a radiation therapy apparatus that irradiates a target region of an irradiated body with radiation, and the radiation therapy planning apparatus. The radiation therapy planning apparatus calculates irradiation dose distribution of the radiation, and includes a data server that transmits a parameter relating to an irradiation condition for obtaining a prescription quantity to the radiation therapy apparatus.

Advantageous Effects of Invention

According to the present invention, it is possible to realize a radiation therapy planning apparatus, a radiation therapy planning method, and a radiation therapy system that enable to perform dose calculation at a high speed and with high accuracy, in a radiation therapy of a scanning irradiation method.

BRIEF DESCRIPTION OF DRAWINGS

FIG. 1 is a diagram illustrating a flow of processing operation in making a radiation therapy plan.

FIG. 2 is a diagram illustrating a flow of a method for searching for an irradiation quantity by a spot scanning method.

FIG. 3 is a diagram illustrating operation which is performed by a radiation therapy planning apparatus according to one embodiment of the present invention.

FIG. 4 is a diagram illustrating a whole configuration of a particle beam therapy system in which a particle beam irradiation apparatus is connected to the radiation therapy planning apparatus.

FIG. 5 is a diagram illustrating a screen view of a target region or the like on a CT screen.

FIG. 6 is a procedure of dose calculation in the radiation therapy planning apparatus according to one embodiment of the present invention, and is a diagram describing a flow of the dose calculation by a simplified Monte Carlo algorithm.

FIG. 7 is a diagram describing a change in a track direction of particles depending on scattering.

FIG. 8 is a diagram illustrating an example of an integrated depth dose table.

FIG. 9 is a diagram illustrating an example of a particle number decreasing rate table.

FIG. 10 is a diagram describing voxel disposition at the time of making the particle number decreasing rate table.

FIG. 11 is a graph illustrating horizontal direction dose distribution of a proton beam which is calculated by the radiation therapy planning apparatus according to one embodiment of the present invention.

FIG. 12 is an outline diagram of a voxel where the horizontal direction dose distribution of the proton beam illustrated in FIG. 11 is obtained.

FIG. 13 is a graph illustrating integrated depth dose distribution that is calculated by the simplified Monte Carlo algorithm, and is a diagram of a case where correction is not performed depending on the particle number decreasing rate table.

FIG. 14 is a graph illustrating the integrated depth dose distribution that is calculated by the simplified Monte Carlo algorithm which is corrected depending on a particle decreasing rate table, in one embodiment of the present invention.

DESCRIPTION OF EMBODIMENTS

Hereinafter, embodiments of the present invention will be described with reference to the accompanying drawings.

EMBODIMENTS

One embodiment of the present invention will be mainly described with reference to FIG. 1 to FIG. 5. One embodiment of the present invention is a radiation therapy planning apparatus that makes a therapy plan of a radiation therapy (particle beam therapy) by a scanning irradiation method.

FIG. 1 is a diagram illustrating a flow of processing operation in making a radiation therapy plan. FIG. 2 is a diagram illustrating a flow of a method for searching for an irradiation quantity to an irradiated body by a spot scanning method. FIG. 3 is a diagram illustrating operation which is performed by the radiation therapy planning apparatus according to one embodiment of the present invention. FIG. 4 is a diagram illustrating a whole configuration of a particle beam therapy system in which a particle beam irradiation apparatus is connected to the radiation therapy planning apparatus. FIG. 5 is a diagram illustrating a screen of a target region or the like on a CT screen.

The spot scanning method is a method in which after a certain point is irradiated with a beam of a specified quantity, the beam is stopped once, and after the beam is moved to the next point to be irradiated, the irradiation is started again. In the scanning irradiation, there is a raster method, in addition to the spot scanning method. The raster method is a method in which the beam is not stopped even in the middle of an irradiation position movement. The present invention can be also applied to the raster method. Moreover, the present invention can be also applied to a scatterer irradiation method in which a scatterer is combined with a ridge filter or a range modulation wheel.

As illustrated in FIG. 4, the radiation therapy planning apparatus includes a display apparatus 401, an input apparatus 402, an arithmetic processing apparatus 403, a memory 404, and a data server 405. The data server 405 is connected to a particle beam irradiation apparatus 406.

Dose distribution or the like of which arithmetic operation is performed by the arithmetic processing apparatus 403 is transmitted to the particle beam irradiation apparatus 406 from the data server 405. The arithmetic processing apparatus 403 includes an optimization calculation unit 4030, a dose calculation unit 4031, and a control unit 4032.

The memory 404 includes a particle number decreasing rate table 4014, and an integrated dose distribution table 4042.

The particle beam irradiation apparatus 406 includes an incidence unit 4061 that generates a proton beam and accelerates the proton beam at an initial stage, an acceleration unit 4062 that accelerates the proton beam, and an irradiation control unit 4063 that shapes the proton beam and controls the irradiation.

An operator inputs a region to be specified per slice of CT image of an irradiated body onto a region input screen of the display apparatus 401, by using a device such as a mouse which is equivalent to the input apparatus 402. If the inputting is finished in each slice, the operator registers the input region. By registering the region, the region which is input by the operator is stored in the memory 404 as three-dimensional position information.

In a case where there is a region that is necessary for evaluation or control else such that an important organ in which an irradiation dose to the irradiated body is suppressed as far as possible is present in the vicinity of the target region, the operator similarly registers a position of the important organ or the like.

FIG. 5 illustrates a state where the operator inputs a target region 501, and important organs 502 and 503 on a certain slice of the CT image in the display apparatus 401 as an example.

The operation illustrated in FIG. 1, and the processing of the apparatus illustrated in FIG. 2 and FIG. 3 responding to the operation will be described.

The operator performs registration instruction operation of the input regions 501, 502 and 503 to the radiation therapy planning apparatus (step 101). As a result, the regions are registered in the therapy planning apparatus, and are stored in the memory 404 (step 301 in FIG. 3).

Subsequently, the operator determines irradiation conditions for the registered target region (step 102 in FIG. 1). That is, the number of irradiation gates, an irradiation direction and the like are determined, based on the positions of the target region and the important organs. All thereof are not determined by the operator, and some are automatically determined by the apparatus.

As in one embodiment of the present invention, in a case where the scanning irradiation method is adopted in the particle beam therapy, not only the irradiation positions of a large number of beams are necessary to be determined, but also energy of each beam, an irradiation interval and the like may be items to be set.

The operator determines a prescription dose for each of the registered regions. If being the prescription dose for the target region, a minimum value and a maximum value of the dose which is received by an inside of the region are input a lot of times, but here, one of the dose with which the target region 501 is irradiated is specified. On the other hand, an allowable dose for the important organ is set a lot of times. In this example, the allowable dose for both of the important organs 502 and 503 is specified.

The irradiation direction, the prescription dose and the like which are set as described above are stored in the memory 404 of the therapy planning apparatus (step 302 in FIG. 3).

Generally, the radiation therapy planning apparatus defines an objective function that quantifies a deviation from the prescription dose (step 303 in FIG. 3), and a residual parameter is calculated by minimizing the value with iterative calculation (step 304 in FIG. 3).

In the step 304, the dose calculation unit 4031 of the arithmetic processing apparatus 403 performs dose distribution calculation by using a simplified Monte Carlo algorithm (which is described later) in one embodiment of the present invention, and the result data thereof is stored in the memory 404. Therefore, per iterative calculation, the dose distribution result data which is stored in the memory 404 is read out, and the parameter is calculated by using the objective function. The iterative calculation and the readout of the data from the memory 404 are performed depending on a command from the control unit 4032. The definition of the objective function and the execution of the calculation are performed by the optimization calculation unit 403 of the arithmetic processing apparatus 403.

In the case where the spot scanning irradiation method is adopted as in one embodiment of the present invention, there is an irradiation quantity (spot irradiation quantity) to each spot as a parameter which is calculated by using the objective function.

Here, a method for searching for the parameter by using the objective function will be described as an example with reference to FIG. 2. In the method for searching for the parameter by using the objective function, a limit condition is set from the information of the prescription dose or the important organ which is set by the operator (step 201 in FIG. 2). Subsequently, the radiation therapy planning apparatus respectively sets m points and n points for calculating the dose within the target region and within the important organ, and makes the objective function based on the limit condition (step 202 in FIG. 2).

A vector of which elements are dose values at m points within the target region is assumed to be $d^{(1)}$, and a relationship between $d^{(1)}$ and a vector x having the spot irradiation quantity as an element is expressed by the following mathematical expression (1).

[Math. 1]

$$d^{(1)} = Ax \qquad (1)$$

In the mathematical expression (1), a matrix A expresses a dose (dose matrix) that is given to a calculation point within the target region from the beam with which each spot is irradiated, and is calculated based on the irradiation direction and the information in the body depending on the CT image.

Similarly, a vector of which elements are dose values at n points within the important organ is assumed to be $d^{(2)}$, and it is possible to express $d^{(2)} = Bx$. B is a matrix which is similar to the matrix A.

In a case where a dose value p which becomes an aim with respect to m points responding to the target region, and an allowable dose value 1 for n points responding to the important organ are set as a limit condition in the step 201, an objective function F(x) is set as the following mathematical expression (2).

[Math. 2]

$$F(x) = \sum_{i=1}^{m} w_i^{(1)}(d_i^{(1)} - p)^2 + \sum_{i=1}^{n} w_i^{(2)}(d_i^{(2)} - l)^2 \theta(d_i^{(2)} - l) \quad (2)$$

In the mathematical expression (2), $W_i^{(1)}$ and $W_i^{(2)}$ are respectively weighted in response to the points, and are values that are input by the operator along with the prescription dose.

A first term of the mathematical expression (2) is a portion that is equivalent to the target region, and the closer the dose value at m points is to the prescription dose value p which is set as an aim, the smaller the objective function F(x) becomes. A second term of the mathematical expression (2) is a term relating to the important organ, and is favorable so long as the value thereof is the dose which does not exceed the allowable dose 1. $\theta(d_i^{(2)}-1)$ of the mathematical expression (2) is a step function, and the value thereof becomes 0 in a case of $d_i^{(2)}<1$, and becomes 1 in other cases.

After the objective function F(x) of the mathematical expression (2) is generated, the radiation therapy planning apparatus repeats the iterative calculation until an end condition of the iterative calculation is satisfied, and thereby searching for x in a case where the objective function F(x) becomes the smallest (step 203 in FIG. 2).

If the process reaches to the end condition (steps 203 and 204 in FIG. 2), the radiation therapy planning apparatus ends the iterative calculation (steps 204 and 205 in FIG. 2).

As described above, indicators such as the calculation time, the number of performing the calculation, and a change quantity of the objective function are set in the end condition.

In the operation flow of FIG. 3, the radiation therapy planning apparatus calculates the dose distribution based on the spot irradiation quantity which is finally obtained as a result of the iterative calculation, and displays the result thereof on the display apparatus 401 (step 305 in FIG. 3). The calculation of the dose distribution in the step 305 is also performed by using the simplified Monte Carlo algorithm (which is described later) in one embodiment of the present invention. In the dose calculation unit 4031, the dose which is assigned to the target region of a detected body is calculated, but the assigned dose is calculated by multiplying the value that is referred from the integrated dose distribution table described later by a reciprocal of a particle decreasing rate table. Thereby, it is possible to correct an influence due to the decrease in the number of particles.

The operation described above responds to the irradiation quantity search of the step 103 in FIG. 1. If the operator determines that the dose distribution which is obtained as a result of the iterative calculation satisfies the condition specified as a prescription dose, the condition is fixed, and is stored in the memory 404 depending on the command of the operator (steps 104 and 105 in FIG. 1).

On the other hand, in the step 104 in FIG. 1, if the operator determines that the condition is not satisfied, for example, in a case where a region that is greatly different from the prescription dose is confirmed, the process returns to the step 102, and there is a need to change the irradiation condition, and to correct the plan.

Next, a dose calculation procedure in the radiation therapy planning apparatus according to one embodiment of the present invention will be described with reference to FIG. 6. This is the processing that is executed by the dose calculation unit 4031 of the arithmetic processing apparatus 403.

In one embodiment of the present invention, the dose calculation is executed by using the simplified Monte Carlo algorithm, but a decreasing rate of the number of particles (decreasing rate of the radiation) in a beam track direction is calculated and tabulated in advance. By using a particle number decreasing rate table (radiation decreasing rate table) 4041, it is possible to execute the dose calculation at a high speed and with high accuracy in contemplation of large-angle scattering, by the simplified Monte Carlo algorithm.

Hereinafter, the dose calculation procedure will be described in detail.

In FIG. 6, first, the radiation therapy planning apparatus disposes a voxel V on a virtual space (step 601). The voxel V has a density ρ, an average atomic number Z, an average atomic mass A, and a dose D at a position x on the CT image in a case where the dose calculation is executed, as an element. An initial value of the dose D is 0.

Next, the radiation therapy planning apparatus generates beam particles on the virtual space. The particle has elements of a position X, a track direction dX, a water equivalent residual range R, an energy E, a water equivalent track length L from a place of the generation. At the time of the generation, initial values $X_0$, $dX_0$, $R_0$ and $E_0$ are given based on the irradiation condition which is set in advance or properties which are peculiar to a particle beam therapy facility. Moreover, an initial value $L_0$ of the water equivalent track length L is 0 (step 602).

A voxel including the particles of the current position $X_k$ is assumed to be $V_k$, and hereinafter, the procedure of transport calculation of the particles will be described.

The particle therapy planning apparatus calculates a next arrival position $X_{k+1}$ of the particle, and a water equivalent track length $L_{k+1}$ at the next arrival position $X_{k+1}$ by using a track direction $dX_k$ and the current position $X_k$ of the particle, and the following mathematical expressions (3) and (4) (step 603).

$$X_{k+1}=X_k+dL \times dX_k \quad (3)$$

$$L_{k+1}=L_k+dL \times WED \quad (4)$$

In the mathematical expressions (3) and (4), dL is a spatial length (step length) between $X_k$ and $X_{k+1}$. Moreover, dL can be determined based on a mean free path of (depending on the density ρ, the average atomic number Z, the average atomic mass A of the voxel $V_k$, and the energy $E_k$ of the particle) of the particle among the voxels $V_k$. WED is a water equivalent thickness ratio of the voxel. There is a case where dL is a fixed value, but in one embodiment of the present invention, dL is assumed to be a length until the particle arrives at a boundary of the voxel, for the simplification of the description.

Next, the radiation therapy planning apparatus calculates a change in the track direction of the particle by multiple Coulomb scattering. The radiation therapy planning apparatus generates a Gaussian distribution-shaped random number of a central value 0 rad and a standard deviation $\theta_0$, and calculates a scattering angle θ' in a θ direction illustrated in FIG. 7. Here, the standard deviation $\theta_0$ is calculated by the radiation therapy planning apparatus, based on the average atomic number Z, the average atomic mass A and the density $\rho$ of the voxel $V_k$, and the energy E and the step length dL of the particle.

A uniform random number of $\pm 2$ $\pi$rad is generated, and a scattering angle $\phi'$ of a $\phi$ direction is calculated. Furthermore, a track direction $dX_k'$ of the particle after the multiple Coulomb scattering is calculated from the track direction $dX_k$, and the calculated $\theta'$ and $\phi'$ (step 604).

Next, the radiation therapy planning apparatus calculates a probability of the large-angle scattering of the particles due to elastic scattering with an atomic nucleus, based on the reaction cross section data which is registered in the memory 404 in advance. Furthermore, the random number is generated, and a need to calculate the change in the track direction of the particle by the large-angle scattering is determined (step 605). In a case of determining that there is no need, the dose calculation procedure proceeds to a step 608.

In the step 605, in a case of determining that there is a need to calculate the large-angle scattering, the radiation therapy planning apparatus proceeds with the processing of calculating the change in the track direction of the particle by the large-angle scattering. In a case of the elastic scattering, first, the radiation therapy planning apparatus obtains probability distribution of an energy loss quantity dE of the particle due to the large-angle scattering, based on the average atomic number Z, the average atomic mass A and the water equivalent thickness ratio $\rho$ of the voxel $V_k$, and the energy $E_k$ of the particle, and determines the energy loss quantity dE of the particle where the random number is generated. Furthermore, the radiation therapy planning apparatus calculates a scattering angle $\theta$ of the $\theta$ direction based on kinematics from the determined energy loss quantity dE. The uniform random number of $\pm 2$ ?Grad is generated, and a scattering angle $\phi$ of the $\phi$ direction is calculated. From the track direction $dX_k'$ and the calculated $\theta$ and $\phi$, the track direction $dX_{k+1}$ of the particle at the next arrival position $X_{k+1}$ of the particle is calculated (step 606).

The radiation therapy planning apparatus according to one embodiment of the present invention uses a calculation model in which the scattering angle $\theta$ is obtained after the energy loss quantity dE is calculated, but a similar effect is obtained even in a case of using a model in which the probability distribution of the scattering angle $\theta$ is obtained based on the average atomic number Z, the average atomic mass A and the water equivalent thickness ratio $\rho$ of the voxel $V_k$, and the energy $E_k$ of the particle, and the scattering angle of the particle where the random number is generated is determined, and finally, the energy loss quantity dE is calculated based on kinematics.

In a case of the inelastic scattering, the radiation therapy planning apparatus calculates an end state of the scattering by using the average atomic number Z, the average atomic mass A and the density $\rho$ of the voxel $V_k$, and the energy $E_k$ of the particle, and obtains the energy loss quantity dE by the track direction $dX_{k+1}$ of the particle at the next arrival position $X_{k+1}$ of the particle and the scattering.

Next, the therapy planning apparatus calculates a new energy $E_k'$ of the particle by $E_k'=E_k-dE$. By using that the energy E and the residual range R have a relationship of one to one, a new residual range $R_k'$ is calculated from the energy $E_k'$ (step 607).

Next, the radiation therapy planning apparatus calculates a dose $D_k$ of the voxel $V_k$. The radiation therapy planning apparatus respectively pulls out an integrated dose value $IDD_k$, and a particle number decreasing rate $C_k$, from the integrated dose distribution table and the particle number decreasing rate table which are registered in advance, by using the water equivalent track length $L_k$ of the particle as a factor.

Furthermore, $IDD_k \times C_k \times dL \times WED$ is added to the dose $D_k$ (step 608). FIG. 8 is a diagram illustrating an example of the integrated depth dose table 4042. FIG. 9 is a diagram illustrating an example of the particle number decreasing rate table 4041. A vertical axis of FIG. 8 indicates the integrated dose, and a horizontal axis thereof indicates the water equivalent track length. Moreover, a vertical axis of FIG. 9 indicates the particle number decreasing rate, and a horizontal axis thereof indicates the water equivalent track length.

Next, the radiation therapy planning apparatus calculates a residual range $R_{k+1}$ of the particle at the next arrival position $X_{k+1}$ from a mathematical expression of $R_{k+1}=R_{k+1}'-dL \times WED$. By using that the energy E and the residual range R have the relationship of one to one, an energy $E_{k+1}$ at the next arrival position $X_{k+1}$ is calculated from the residual range $R_{k+1}$ (step 609).

Next, the radiation therapy planning apparatus determines the end of the particle calculation. In the embodiment, the calculation of the particle is ended in a case where the residual range $R_{k+1}$ is 0 or less, or in a case where the position $X_{k+1}$ of the particle is on an outside of all voxels (step 610). Furthermore, in a case where the condition is not satisfied, the transport calculation is carried out with the similar steps, towards a next arrival position $X_{k+2}$.

If the calculation relating to all particles which are set in advance is ended, the radiation therapy planning apparatus stores the dose D of each voxel in the memory 404, and ends the dose calculation (steps 611 and 612). Furthermore, the value is displayed on the display apparatus 501 as dose distribution. The dose of the voxel through which the particle is not passed at all becomes 0.

FIG. 10 is a diagram describing the voxel disposition at the time of making the particle number decreasing rate table. As illustrated in FIG. 10, the particle number decreasing rate table is calculated under the condition where a voxel 407 that is configured of a uniform medium (for example, water) is irradiated with an infinitesimal beam of emittance zero. The voxel 407 has a sufficient size in a direction perpendicular to the beam track direction, and is disposed in the beam track direction.

At the time of making the particle number decreasing rate table 4041, instead of $IDD_k \times C_k \times dL \times WED$, dL is added to the dose D of each voxel, in the step 608 (FIG. 6) of the transport calculation described above. After the calculation is ended, if the obtained dose D is divided by a total number of calculated particles, the particle number decreasing rate table 4041 relating to the water equivalent track length L is obtained.

FIG. 11 is a graph illustrating horizontal direction dose distribution of the proton beam which is calculated by the radiation therapy planning apparatus according to one embodiment of the present invention, and FIG. 12 is an outline diagram of the voxel 407 where the horizontal direction dose distribution of the proton beam illustrated in FIG. 11 is obtained. A vertical axis of FIG. 11 indicates the dose, and a horizontal axis thereof indicates the position of the horizontal direction. As illustrated in FIG. 11, a distant component due to the large-angle scattering is reproduced.

FIG. 13 is a graph illustrating the integrated depth dose distribution that is calculated by the simplified Monte Carlo algorithm, and is that of a case where correction is not performed depending on the particle number decreasing rate table 4041. FIG. 14 is a graph illustrating the integrated depth dose distribution that is calculated by the simplified Monte Carlo algorithm which is corrected depending on the particle number decreasing rate table 4041, in one embodiment of the present invention. In FIG. 13 and FIG. 14, a circle indicates a calculation result, and a solid line indicates the data of the integrated dose distribution table 4042 which is registered in the radiation therapy planning apparatus. If the graph illustrated in FIG. 13 is compared with the graph illustrated in FIG. 14, as illustrated in FIG. 14, it is possible to understand that the value which is referred from the integrated depth dose table 4042 is corrected by using the particle number decreasing rate table 4041, and thereby, the decrease of the dose is suppressed.

That is, according to one embodiment of the present invention, the depth dose distribution data which is calculated by the simplified Monte Carlo algorithm is multiplied by the reciprocal of the particle decreasing rate distribution data, and the irradiation dose is determined, and thereby, it is possible to perform the dose calculation with high accuracy.

According to the present invention, it is possible to perform the dose calculation at a high speed, in comparison with a normal Monte Carlo algorithm in which the calculation is obtained by using a theoretical expression or an empirical expression. That is, since the dose that is assigned per step refers to the integrated depth dose distribution (Integrated depth dose, IDD) of the beam which is recorded in the therapy planning apparatus, it is possible to perform the dose calculation at a high speed, in comparison with the normal Monte Carlo algorithm in which the calculation is obtained by using the theoretical expression or the empirical expression. Such a calculation method is valid in the simplified Monte Carlo algorithm because the number of particles is stored with respect to the beam track direction on a water equivalent thickness space. The integrated depth dose of the beam is obtained by measurement using a large-sized parallel plate ionization chamber, and is registered in the therapy planning apparatus in advance.

In other words, according to the present invention, it is possible to realize the radiation therapy planning apparatus that enables to perform the dose calculation at a high speed and with high accuracy by using the simplified Monte Carlo algorithm, in the therapy planning apparatus of the scanning irradiation method.

Moreover, according to the present invention, it is possible to realize the radiation therapy planning method that enables to perform the dose calculation at a high speed and with high accuracy by using the simplified Monte Carlo algorithm, in the therapy planning method of the scanning irradiation method.

As illustrated in FIG. 4, if the radiation therapy planning apparatus of the present invention is connected to the particle beam irradiation apparatus or is inserted into the particle beam irradiation apparatus, it is possible to perform the particle beam irradiation by the dose calculation at a high speed and with high accuracy.

Therefore, according to the present invention, it is possible to realize the particle beam therapy system that enables to perform the particle beam irradiation by the dose calculation at a high speed and with high accuracy, and enables to improve a throughput.

The example described above is an example in which the present invention is applied to the radiation therapy planning apparatus, the radiation therapy planning method, and the particle beam therapy system, but the present invention is not limited to the particle beam, and can be applied to other radiation therapy planning apparatuses, other radiation therapy planning methods, and other radiation therapy systems.

REFERENCE SIGNS LIST

401: DISPLAY APPARATUS, 402: INPUT APPARATUS, 403: ARITHMETIC PROCESSING APPARATUS, 404: MEMORY, 405: DATA SERVER, 4030: OPTIMIZATION CALCULATION UNIT, 4031: DOSE CALCULATION UNIT, 4032: CONTROL UNIT, 4041: PARTICLE BEAM DECREASING RATE TABLE, 4042: INTEGRATED DOSE DISTRIBUTION TABLE, 4061: INCIDENCE UNIT, 4062: ACCELERATION UNIT, 4063: IRRADIATION CONTROL UNIT

The invention claimed is:

1. A radiation therapy planning apparatus, using a simplified Monte Carlo algorithm for calculating a dose to be assigned to particles by referring to an integrated dose distribution table, comprising:
   an input device to input a target region and a prescription dose of an irradiated body which is to be irradiated with radiation;
   a memory storing a radiation decreasing rate table indicating a relationship between a track length of the radiation to the irradiated body and a decreasing rate of the radiation; and
   a processor coupled with the input device and the memory that is configured to calculate dose distribution by using the simplified Monte Carlo algorithm based on the target region and the prescription dose of the irradiated body and correct the calculated dose distribution by using the decreasing rate of the radiation of the radiation decreasing rate table stored in the memory,
   wherein the calculated dose distribution is stored in the memory.

2. The radiation therapy planning apparatus according to claim 1,
   wherein the processor is further configured to calculate, by using an objective function, an irradiation condition which minimizes a difference between the calculated dose distribution and the prescription dose.

3. The radiation therapy planning apparatus according to claim 1, further comprising:
   a display to display the dose distribution which is calculated and corrected by the processor.

4. The radiation therapy planning apparatus according to claim 1,
   wherein the radiation is a particle beam.

5. The radiation therapy planning apparatus according to claim 1,
   wherein the processor is further configured to calculate the dose to be assigned to the particles by multiplying a reciprocal of the decreasing rate of the radiation and a value referred from the integrated dose distribution table.

6. The radiation therapy planning apparatus according to claim 1,
   wherein the processor is further configured to calculate the dose to be assigned to the particles by using the decreasing rate of the radiation in case that the particles are scattered at a large angle, and
   wherein the processor calculates the doses to be assigned to the particles without the decreasing rate of the radiation in a case that the particles are not scattered at a large angle.

7. A radiation therapy planning method, using a simplified Monte Carlo algorithm for calculating a dose to be assigned to particles by referring to an integrated dose distribution table, comprising:

inputting a target region and a prescription dose of an irradiated body which is to be irradiated with radiation;

storing, in a memory, a radiation decreasing rate table indicating a relationship between a track length of the radiation to the irradiated body and a decreasing rate of the radiation;

calculating dose distribution by using the simplified Monte Carlo algorithm based on the target region and the prescription dose of the irradiated body and correcting the calculated dose distribution by using the decreasing rate of the radiation of the radiation decreasing rate table stored in the memory; and storing the calculated dose distribution in the memory.

8. The radiation therapy planning method according to claim 7, further comprising:

calculating, by using an objective function, an irradiation condition which minimizes a difference between the calculated dose distribution and the prescription dose.

9. The radiation therapy planning method according to claim 7, further comprising:

displaying the calculated and corrected dose distribution by a display unit.

10. The radiation therapy planning method according to claim 7, wherein the radiation is a particle beam.

11. A radiation therapy system, using a simplified Monte Carlo algorithm for calculating a dose to be assigned to particles by referring to an integrated dose distribution table, comprising:

a radiation therapy apparatus that irradiates a target region of an irradiated body with radiation according to a dose distribution; and a radiation therapy planning apparatus that calculates irradiation dose distribution of the radiation in the radiation therapy apparatus, and performs planning of a radiation therapy, wherein the radiation therapy planning apparatus includes, an input device to input a target region and a prescription dose of an irradiated body which is to be irradiated with radiation;

a memory storing a radiation decreasing rate table indicating a relationship between a track length of the radiation to the irradiated body and a decreasing rate of the radiation; and a processor coupled with the input device and the memory that is configured to calculate dose distribution by using the simplified Monte Carlo algorithm based on the target region and the prescription dose of the irradiated body and correct the calculated dose distribution by using the decreasing rate of the radiation of the radiation decreasing rate table stored in the memory, wherein the radiation therapy planning apparatus transmits the calculated dose distribution to the radiation therapy apparatus.

12. The radiation therapy system according to claim 11, wherein the processor is further configured to calculate by using an objective function, an irradiation condition which minimizes a difference between the calculated dose distribution and the prescription dose.

13. The radiation therapy system according to claim 11, further comprising:

a display to display the dose distribution which is calculated and corrected by the processor of the radiation therapy planning apparatus.

14. The radiation therapy system according to claim 11, wherein the radiation is a particle beam.

* * * * *